United States Patent
Gueret et al.

(10) Patent No.: US 9,011,394 B2
(45) Date of Patent: Apr. 21, 2015

(54) SHEET STRUCTURE HAVING AT LEAST ONE COLORED SURFACE

(75) Inventors: Jean-Louis Gueret, Paris (FR); Montserrat Tugas Casanoves, Paris (FR)

(73) Assignee: L'Oreal, Paris (FR)

( * ) Notice: Subject to any disclaimer, the term of this patent is extended or adjusted under 35 U.S.C. 154(b) by 1639 days.

(21) Appl. No.: 11/790,403

(22) Filed: Apr. 25, 2007

(65) Prior Publication Data

US 2008/0029121 A1 Feb. 7, 2008

Related U.S. Application Data

(60) Provisional application No. 60/799,356, filed on May 11, 2006.

(30) Foreign Application Priority Data

Apr. 25, 2006 (FR) ..................................... 06 51463

(51) Int. Cl.
*A45D 33/34* (2006.01)
*A61K 8/02* (2006.01)
(Continued)

(52) U.S. Cl.
CPC .............. *A61K 8/0212* (2013.01); *A61K 8/0237* (2013.01); *A61K 9/703* (2013.01); *A61K 2800/43* (2013.01); *A61Q 19/00* (2013.01); *B32B 5/30* (2013.01); *B32B 5/022* (2013.01);
(Continued)

(58) Field of Classification Search
CPC ................... B32B 2260/025; B32B 2260/046; B32B 2262/0261; B32B 2262/0276; B32B 2262/04; B32B 2262/06; B32B 2264/02; B32B 2264/10; B32B 2264/101; B32B 2307/407
See application file for complete search history.

(56) References Cited

U.S. PATENT DOCUMENTS 5,503,076 A * 4/1996 Yeo ................................ 101/483
5,658,642 A * 8/1997 Strongwater .................. 428/161
(Continued)

FOREIGN PATENT DOCUMENTS

DE 101 49 908 A1 4/2003
DE 103 22 444 A1 10/2003
(Continued)

OTHER PUBLICATIONS

U.S. Appl. No. 09/240,603 (Available As Prior Art As of Jul. 16, 2002, the date of publication of U.S. Patent No. 6,419,935, which incorporates by reference U.S. Appl. No. 09/240,603).*

*Primary Examiner* — Bethany Barham
*Assistant Examiner* — Dominic Lazaro
(74) *Attorney, Agent, or Firm* — Oliff PLC

(57) ABSTRACT

The present invention relates to a sheet structure for application to a region of the human body, including the face, the structure comprising:
 a colored matrix;
 a first substrate situated on a first side of the matrix, a first surface of the sheet structure being defined by the first substrate; and
 a second substrate situated on a second side of the matrix, opposite the first, a second surface of the sheet structure being defined by the second substrate;
the first and second substrates having different opacities, and at least one of the first and second substrates having an opacity that is low enough to enable the subjacent colored matrix to show through in such a manner that the first and second surfaces of the matrix appear to be of different colors.

21 Claims, 1 Drawing Sheet

(51) Int. Cl.
*A61K 9/70* (2006.01)
*A61Q 19/00* (2006.01)
*B32B 5/30* (2006.01)
*B32B 5/02* (2006.01)
*B32B 5/16* (2006.01)
*B32B 5/24* (2006.01)
*B32B 7/02* (2006.01)
*B32B 27/30* (2006.01)
*B32B 29/02* (2006.01)
*B32B 29/06* (2006.01)

(52) U.S. Cl.
CPC .. *B32B 5/16* (2013.01); *B32B 5/24* (2013.01); *B32B 7/02* (2013.01); *B32B 27/308* (2013.01); *B32B 29/02* (2013.01); *B32B 29/06* (2013.01); B32B 2260/025 (2013.01); B32B 2260/046 (2013.01); B32B 2262/0261 (2013.01); B32B 2262/0276 (2013.01); B32B 2262/04 (2013.01); B32B 2262/06 (2013.01); B32B 2264/02 (2013.01); B32B 2264/10 (2013.01); B32B 2264/101 (2013.01); B32B 2307/402 (2013.01); B32B 2307/41 (2013.01); B32B 2307/72 (2013.01); B32B 2555/00 (2013.01); *A61K 8/0241* (2013.01)

(56) References Cited

U.S. PATENT DOCUMENTS

| | | | | |
|---|---|---|---|---|
| 5,830,485 | A | * | 11/1998 | Gueret et al. ................ 424/401 |
| 6,015,605 | A | * | 1/2000 | Tsujiyama et al. ........ 428/195.1 |
| 6,419,935 | B1 | * | 7/2002 | Gueret ........................ 424/401 |
| 2001/0024656 | A1 | * | 9/2001 | Dillon ......................... 424/443 |
| 2004/0191198 | A1 | * | 9/2004 | Hochstein et al. .............. 424/63 |
| 2007/0277806 | A1 | * | 12/2007 | Dodo ....................... 126/263.02 |

FOREIGN PATENT DOCUMENTS

| | | | | |
|---|---|---|---|---|
| EP | 0 628 300 | A1 | 12/1994 | |
| EP | 0 933 067 | B1 | 8/1999 | |
| EP | 0 933 077 | A1 | 8/1999 | |
| EP | 1043 018 | A1 | 10/2000 | |
| EP | 1 129 702 | A1 | 9/2001 | |
| WO | WO 00/33796 | A1 | 6/2000 | |
| WO | WO 03/045345 | A1 | 6/2003 | |
| WO | WO 2006/006655 | A1 * | 1/2006 | ............... A61F 7/08 |
| WO | WO 2006006655 | A1 * | 1/2006 | |

* cited by examiner

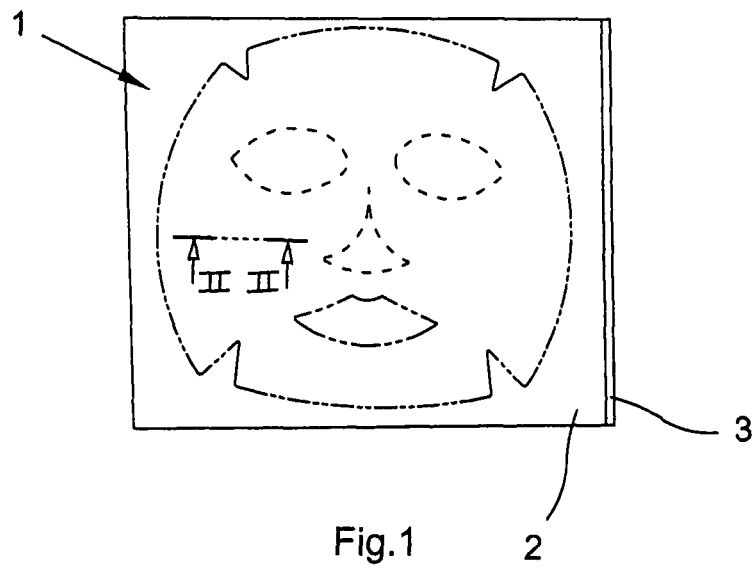
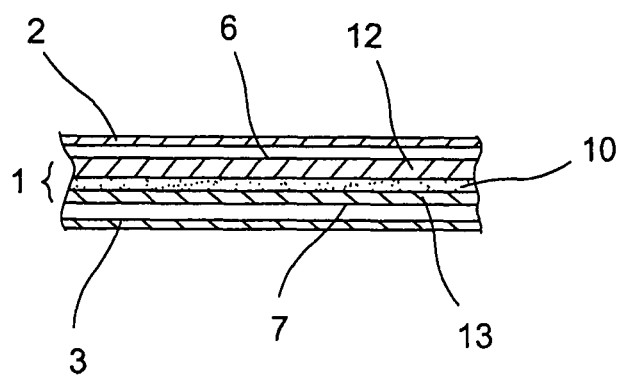
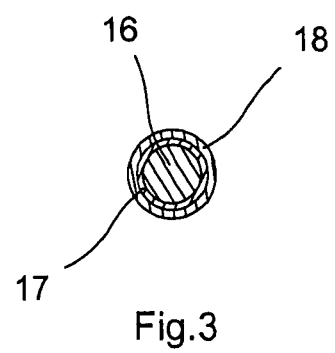
Fig.1
Fig.2
Fig.3

SHEET STRUCTURE HAVING AT LEAST ONE COLORED SURFACE

This non provisional application claims the benefit of French Application No. 06 51463 filed on Apr. 25, 2006 and U.S. Provisional Application No. 60/799,356 filed on May 11, 2006.

The present invention relates to sheet structures, such as masks or patches, for application to a region of the human body, including the face.

BACKGROUND

European patent application EP 1 129 702 discloses a composite structure having an adhesive matrix that is situated between two support layers that can be constituted by non-woven fabrics. Such a structure can be wetted before use, and then one of its surfaces can be applied to the skin, so as to release onto said skin at least one active ingredient contained in the matrix.

When the structure is asymmetrical, it can be necessary to indicate to the user which surface is the application surface.

To do this, one solution can consist in coloring one of the support layers.

However, the non-woven fabric sheets generally proposed by manufacturers are white, and the production of a colored non-woven fabric can turn out to be expensive when the quantities required are relatively small.

SUMMARY

There exists a need to benefit from a means for making it possible to distinguish between the two surfaces of a sheet structure, and that is relatively inexpensive and simple to implement.

European patent EP 0 933 067 B1 discloses a cleansing patch, for revealing the state of the skin, said patch comprising a colored polymeric matrix for application to the skin.

European patent application EP 1 043 018 A1 discloses a magnetic patch that is suitable for containing a colored layer, and that includes a matrix for application to the region to be treated.

Those prior-art embodiments do not provide a solution to the problem of identifying the surfaces of a sheet structure when the matrix does not come directly into contact with the region to be treated, but is sandwiched between two layers of at least one substrate.

Exemplary embodiments of the invention provide a sheet structure for application to a region of the human body, including the face, the structure comprising:
  a colored matrix;
  a first substrate situated on a first side of the matrix, a first surface of the sheet structure being defined by the first substrate; and
  a second substrate situated on a second side of the matrix, opposite the first, a second surface of the sheet structure being defined by the second substrate.

The first and second substrates are permanently bound to the matrix. Accordingly, the first and second substrates are present after application to the materials to be treated, during use of the structure.

The first and second substrates are each different from a removable protective sheet.

The first and second substrates have different opacities, and at least one of the first and second substrates has an opacity that is low enough to enable the subjacent colored matrix to show through in such a manner that the first and second surfaces of the matrix appear to be of different colors.

The invention enables simple means to be implemented in order to distinguish between the two surfaces of the sheet structure, and thus enables the user to identify the application surface, which is the surface having the stronger color.

In addition, if so desired, the invention makes it possible to use, as substrates, conventional white non-woven fabrics, while giving the user the impression that at least one of the substrates is colored, e.g. red, green, blue, yellow, orange, pink, purple, to mention but a few hues.

The invention also makes it possible to diversify the appearance of sheet structures by acting on the color of the matrix, and even to create esthetic effects by using matrices of color that is not uniform.

The matrix is advantageously colored by dispersing colored particles therein. Compared to using a dye, this presents the advantage of reducing the risk of said dye bleeding into the substrates and onto the region being treated.

The particles used may be particles that are coated with a non-opaque outer coating, thereby making it possible to isolate the matrix from the pigments or dyes that are present within the particles. By way of example, the outer coating is a polymerizable or cross-linked material, in particular a transparent or translucent polymer.

Each colored particle may include a core that may be colorless or opaque. By way of example, the core may be constituted by an inorganic material, e.g. glass. The core may be covered by a colored membrane, e.g. a layer of at least one pigment or of a colored polymer. The membrane may include a pigment that is held on the core by means of a binder, said binder being the same polymer as the polymer that constitutes the outer coating, for example.

The colored particles that are dispersed in the matrix are colored glass beads that are coated with a transparent polymer, for example. By way of example, the average size of the colored particles lies in the range 10 micrometers ($\mu$m) to 1000 $\mu$m.

The first substrate may comprise a layer of non-woven fabric, having a density that lies in the range 20 grams per square meter (g/m$^2$) to 100 g/m$^2$, for example.

The second substrate may also comprise a layer of non-woven fabric, having a density that lies in the range 5 g/m$^2$ to 30 g/m$^2$, for example. The non-woven fabric of the first substrate may present a density that is greater than the density of the second substrate.

The sheet structure, that may form a mask or a patch for application to the skin, may be packaged in a protective cover.

BRIEF DESCRIPTION OF THE DRAWINGS

The invention can be better understood on reading the following detailed description of a non-limiting embodiment thereof, and on examining the accompanying drawing, in which:

FIG. 1 is a diagram of a sheet structure of the invention;
FIG. 2 is a section on II-II of FIG. 1; and
FIG. 3 shows, in isolation, a colored particle dispersed in the matrix.

MORE DETAILED DESCRIPTION

FIG. 1 shows a sheet structure 1 that is packaged for example between two protective sheets 2 and 3 that are formed by folding a strip in half, for example.

The sheets 2 and 3 can be constituted by a non-stick paper or film, e.g. a siliconed paper, and they can optionally come into contact with the outside surfaces 6 and 7 of the sheet structure 1. For the purpose of clarity of the drawing, a gap is shown between the protective sheets 2 and 3 and the respective surfaces 6 and 7 in FIG. 2, but the gap need not exist, the surfaces 6 and 7 possibly adhering slightly to the sheets 2 and 3, where appropriate.

The sheet structure 1 includes a colored (non-white) matrix 10 that is disposed between substrates 12 and 13. The matrix 10 permanently adheres to the substrates 12 and 13, which are not intended to be separated from the matrix during use.

Substrates

In accordance with an aspect of the invention, the substrates 12 and 13 are different so as to present opacities that are different, and so as to enable the outside surfaces 6 and 7 to appear to the user to be of different colors, by enabling the matrix 10 to show through to a greater or lesser extent.

By way of example, the substrate 12 presents a thickness and/or a weight that is greater than the thickness and/or the weight of the substrate 13, so as to enable the surface 7 to be more strongly colored than the surface 6.

In the absence of the matrix 10, the substrates 12 and 13 can be white.

The substrates 12 and 13 can be selected from non-woven fabrics, inter alia.

The substrates 12 and 13 can be of the same kind, e.g. both being of non-woven fabrics.

The substrates 12 and 13 can be single-layer or multi-layer substrates.

Colored Particles

The matrix 10 can be colored in various ways, and advantageously by incorporating coated colored particles.

FIG. 3 is a diagram showing an example of such a particle. The particle can comprises an inorganic core 16, e.g. a glass bead, that is coated with a colored membrane 17 that is itself coated with a transparent polymer coating 18 for isolating the colored membrane 17 from the matrix 10.

The membrane 17 can contain a polymer binder that causes a pigment to adhere to the core 16, e.g. an iron oxide or any other pigment that is conventionally used in cosmetics, e.g. a pigment that generates a color by an absorption phenomenon.

The coating 18 can be a coating of the same polymer as the polymer that is used as a binder within the membrane 17.

The colored particles can optionally present a spherical shape.

By way of example, the colored particles can be fibers that are colored throughout or fibers that are coated with a pigment and possibly covered by a polymer coating.

By way of example, it is possible to use fibers made of polyamide, polyester, or rayon, or plant fibers, e.g. cotton, corn, wood, or linen.

The quantity of colored particles that are incorporated in the matrix depends on the strength desired for the color, and can lie in the range 0.2% by weight, relative to the total weight of the dry matrix in the sheet structure, for a pastel color, to 10% by weight for a stronger color.

When coated particles are used, the outside coating of the particles can comprise a polymer selected from acrylic polymers, cyanoacrylates, urea formaldehyde resins, polyurethanes, vinyl polymers, and pseudo latex, for example. The coated core can comprise a material other than glass, e.g. selected from carbonates, silica, mica, or sawdust.

The colored particles that are incorporated in the matrix can be substantially the same size, or they can present different sizes in order to obtain speckled effects, for example. The core can be made of an inorganic material other than glass, or it can be made of an organic material.

Where appropriate, it is possible to incorporate different colored particles in the matrix so as to create mottled effects and/or new colors.

Matrix

The matrix can have a polyacrylic or polyvinyl adhesive base.

The matrix can be hydrophobic, e.g. having a silicone polymer base or a polyurethane base of the polyester polyurethane or polyether polyurethane type.

The matrix can also include a hydrogel.

The matrix can contain particles of at least one water-absorbent agent that is dispersed in uniform manner in the matrix. The particles of water-absorbent agent can, by capturing water, encourage a hydrosoluble solid active compound to dissolve.

Amongst the water-absorbent agents that may possibly be present in the polymeric matrix in the dispersed state, mention can be made of superabsorbent cross-linked polyacrylates that swell greatly in water, such as those sold by NORSOLOR under the trade name "Aquakeep®"; polyvinyl alcohol; carboxyvinyl polymers, such as those sold by GOODRICH under the trade names of "Carbopol®"; semi-synthetic derivatives of cellulose, such as carboxymethylcellulose; natural substances such as starches, natural gums (guar gum, gum Arabic, adragant gum), casein, phycocolloids (carragenates, alginates, agar-agar), cotton fibers, and gelatin.

Active Ingredients

The sheet structure can contain at least one active ingredient.

The active ingredient, used alone or in combination, can be selected from conventionally used hydrophilic active ingredients such as antioxidants, free-radical scavengers, moisturizers, depigmenting agents, liporegulators, anti-acne agents, antidandruff agents, anti-ageing agents, softeners, anti-wrinkle agents, keratolytic agents, anti-inflammatories, refreshening agents, cicatrizing agents, vascular protective agents, antibacterials, antifungals, antiperspirants, deodorants, skin conditioners, immunomodulators, and nourishing agents.

In particular, it is possible to use one or more active ingredients selected in particular from ascorbic acid and biologically compatible salts thereof, enzymes, antibiotics such as clindamycin phosphate, components having a tightening effect such as soya or wheat protein powders, α-hydroxy acids and salts thereof, hydroxylated polyacids, sucroses and derivatives thereof, urea, amino acids, oligopeptides, water-soluble plant and yeast extracts, protein hydrolysates such as collagen and elastin, hyaluronic acid, mucopolysaccharides, vitamins B2, B6, H and PP, panthenol, folic acid, acetylsalicylic acid, allantoin, glycyrrhetic acid, kojic acid, hydroquinone, etc.

Where appropriate, the sheet structure can also include at least one liposoluble compound selected from the following compounds: D-α-tocopherol, DL-α-tocopherol, D-α-tocopherol acetate, DL-α-tocopherol acetate, ascorbyl palmitate, vitamin F and vitamin F glycerides, vitamins D, vitamin D2, vitamin D3, retinol, retinol esters, retinol palmitate, retinol propionate, β-carotene, D-panthenol, farnesol, farnesyl acetate; jojoba and blackcurrant oils rich in essential fatty acids; keratolytic agents such as salicylic acid, salts and esters thereof, 5-(n-octanoyl) salicylic acid and esters thereof, alkyl esters of α-hydroxy acids such as citric acid, lactic acid, glycolic acid; asiatic acid, madecassic acid, asiaticoside, total extract of *centella asiatica*, β-glycyrrhetinic acid, α-bisabolol, ceramides such as 2-oleoylamino-1,3-octadecane; phytanetriol, milk sphingomyelin, phospholipids of marine origin rich in polyunsatured essential fatty acids, ethoxyquin;

extract of rosemary, extract of *melissa*, quercetin, extract of dried microalgae, and steroidal anti-inflammatories.

Such active ingredients can be incorporated in the dissolved state in oils, used alone or in combination, amongst which mention can be made of: oils of animal, vegetable, or mineral origin, and in particular animal or vegetable oils formed by fatty acid esters and polyol esters, in particular liquid triglycerides, e.g. sunflower, corn, soya, squash, grape seed, sesame, hazelnut, apricot, almond, or avocado oils; fish oils, glycerol tricaprocaprylate, or $R_1COOR_2$ formula vegetable or animal oils in which $R_1$ represents the higher fatty acid residue having 7 to 19 carbon atoms, and $R_2$ represents a branched hydrocarbon chain having 3 to 20 carbon atoms, e.g. Purcellin oil; oils of wheat germ, calophyllum, sesame, coriander, carthame, *passiflora* oil, oil of *rosa mosqueta*, macadamia nut oil, oils of fruit seed (grape, blackcurrant, orange, kiwi), rapeseed, copra, groundnut, evening primrose, palm, castor, linseed, jojoba, chia, olive, or cereal germ, such as wheat germ oil, rice bran oil, karite oil; acetylglycerides; octanoates, decanoates, or ricinoleates of alcohols or polyalcohols; fatty acid triglycerides; glycerides; paraffin, vaseline oil, perhydrosqualene; fatty alcohols (stearylic alcohol, cetylic alcohol) and fatty acids (stearylic acid) and esters thereof; polyalkyl($C_1$-$C_{20}$) siloxanes and in particular those having a trimethylsilyl end group, preferably those having a viscosity that is less than 0.06 square meters per second ($m^2/s$), amongst which mention can be made of linear polydimethylsiloxanes, and alkylmethylpolysiloxanes such as cetyldimethicone (trade name CTFA). Mention can also be made of partially fluorinated hydrocarbon oils or perfluronianated oils, and in particular perfluoropolyethers and perfluoroalkanes. A liposoluble active compound can also be incorporated in the matrix in powder form.

Use

The sheet structure can be used after having been wetted by a liquid for enabling at least one active ingredient contained in the matrix and/or at least one of the substrates to be transferred onto the skin.

The liquid can be water, an aqueous solution, an oil, an emulsion, an alcohol, an alcohol solution, inter alia.

Where appropriate, the sheet structure can also be applied to a skin that is dry or wet. In an embodiment, perspiration can possibly suffice for wetting the matrix.

Proposed Example

A face mask is made in the following way.

A colored matrix in the fluid state is disposed on a white non-woven fabric weighing 50 $g/m^2$, then a non-woven fabric that is less dense than the first, e.g. weighing 15 $g/m^2$, is couched thereon.

The colored matrix can present the following composition (% by weight).

10% ORGASOL®
15% Superabsorbent polyacrylate
40% Glycerine
8.1% Foaming agent
0.9% Caffeine
24% Acrylic adhesive
2% Colored particles*

*The colored particles can be obtained as follows.

Glass beads of 100 μm in diameter are mixed with an organic pigment and with an isocyanate binder. The beads coated in this way are covered by a 10 μm layer of isocyanate.

A mask is obtained having a pink color that is stronger on the surface to be applied than on the opposite surface.

The mask can be used by being applied to the face after the application surface has been wetted with water.

Although the present invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The expression "comprising a" should be understood as being synonymous with "comprising at least one".

What is claimed is:

1. A cosmetic sheet structure for application to a region of the human body, including the face, the cosmetic sheet structure comprising:
    a colored matrix;
    at least one active ingredient contained in the cosmetic sheet structure and transferrable to the region;
    a first substrate comprising a layer of non-woven fabric having a density in a range of from 20 $g/m^2$ to 100 $g/m^2$, the first substrate being situated on a first side of the matrix, a first surface of the cosmetic sheet structure being defined by the first substrate; and
    a second substrate having a density in a range of from 5 $g/cm^2$ to 30 $g/cm^2$, situated on a second side of the matrix, opposite the first, a second surface of the cosmetic sheet structure being defined by the second substrate;
    wherein the first and second substrates each have an opacity that is low enough to enable the subjacent colored matrix to show through, such that both the opacities and densities of the substrates are different so that the first and second surfaces of the cosmetic sheet structure appear to be of different colors.

2. A cosmetic sheet structure according to claim 1, the substrates being of white non-woven fabrics.

3. A cosmetic sheet structure according to claim 1, the color of the matrix not being uniform.

4. A cosmetic sheet structure according to claim 1, the matrix being colored by colored particles dispersed therein.

5. A cosmetic sheet structure according to claim 4, the colored particles presenting a non-opaque outer coating of a transparent or translucent polymer.

6. A cosmetic sheet structure according to claim 4, each colored particle including a core that is covered by a colored membrane.

7. A cosmetic sheet structure according to claim 6, the core comprising a material selected from glass, carbonates, silica, mica, or sawdust.

8. A cosmetic sheet structure according to claim 6, the membrane containing at least one pigment.

9. A cosmetic sheet structure according to claim 6, the core being inorganic.

10. A cosmetic sheet structure according to claim 5, the colored particles that are dispersed in the matrix comprising colored glass beads that are coated with a transparent polymer.

11. A cosmetic sheet structure according to claim 1, the second substrate comprising a layer of non-woven fabric.

12. A cosmetic sheet structure according to claim 1, forming a mask or a patch for application to skin.

13. A cosmetic sheet structure according to claim 1, being packaged in a protective cover.

14. A cosmetic sheet structure according to claim 1, including at least one cosmetically active ingredient.

15. A cosmetic sheet structure according to claim 1, the matrix being coloured in red, green, blue, yellow, orange, pink or indigo.

16. A cosmetic sheet structure according to claim 1, the at least one active ingredient being contained in the matrix.

17. A cosmetic sheet structure according to claim 1, the at least one active ingredient being contained in the first or second substrate.

18. A cosmetic sheet structure according to claim 1, the at least one active ingredient being transferred to the region when the cosmetic sheet structure is wetted by one of water, an aqueous solution, an oil, an emulsion, an alcohol, and an alcohol solution.

19. A cosmetic sheet structure according to claim 1, one of the first and second surfaces having a more colorfast color than the other of the first and second surfaces, the surface of more colorfast color being for application to the region.

20. A cosmetic sheet structure according to claim 1, the at least one active ingredient being selected from the group consisting of antioxidants, free-radical scavengers, moisturizers, depigmenting agents, liporegulators, anti-acne agents, antidandruff agents, anti-ageing agents, softeners, anti-wrinkle agents, keratolytic agents, anti-inflammatories, refreshening agents, cicatrizing agents, vascular protective agents, antibacterials, antifungals, antiperspirants, deodorants, skin conditioners, immunomodulators, and nourishing agents.

21. A cosmetic sheet structure according to claim 1, the first and second substrates being white.

\* \* \* \* \*